128-24 A    AU 335    EX
12/4/79     XR    4,176,454

United States Patent [19]
Hatter et al.

[11] 4,176,454
[45] Dec. 4, 1979

[54] ULTRASONIC TOOTH CLEANER

[75] Inventors: Edward E. Hatter; Richard H. Taylor, both of Irvine; Richard D. McGunigle, La Habra Heights, all of Calif.

[73] Assignee: Biosonics International, Ltd., Irvine, Calif.

[21] Appl. No.: 790,312

[22] Filed: Apr. 25, 1977

[51] Int. Cl.$^2$ ................................. A61C 3/03
[52] U.S. Cl. .................... 433/119; 128/24 A; 366/127
[58] Field of Search ............. 32/58, DIG. 4; 128/24 A, 62 A; 366/127; 51/59 SS

[56]    References Cited
U.S. PATENT DOCUMENTS

| 2,680,333 | 6/1954 | Calosi | 32/DIG. 4 |
|---|---|---|---|
| 2,917,042 | 12/1959 | Brown et al. | 128/24 A |
| 3,335,443 | 8/1967 | Parisi et al. | 128/24 A |
| 3,380,446 | 4/1968 | Martin | 128/24 A |
| 3,385,291 | 5/1968 | Martin | 128/62 A |
| 3,401,690 | 9/1968 | Martin | 128/24 A |
| 3,466,689 | 9/1969 | Aurelio et al. | 128/62 A |
| 3,488,788 | 1/1970 | Robinson | 128/62 A |
| 3,760,799 | 9/1973 | Crowson | 128/24 A |
| 3,847,662 | 11/1974 | Massa | 128/24 A |

FOREIGN PATENT DOCUMENTS 1100914  9/1955  France ................... 128/24 A

*Primary Examiner*—Louis G. Mancene
*Assistant Examiner*—John J. Wilson
*Attorney, Agent, or Firm*—Nilsson, Robbins, Dalgarn, Berliner, Carson & Wurst

[57]    ABSTRACT

An ultrasonic method and apparatus for removing dental plaque from teeth in situ and for cleaning the teeth employing a liquid couple for imparting ultrasonic energy to the surface of the teeth at ultrasonic energy levels which are not harmful to the teeth or gums.

3 Claims, 3 Drawing Figures

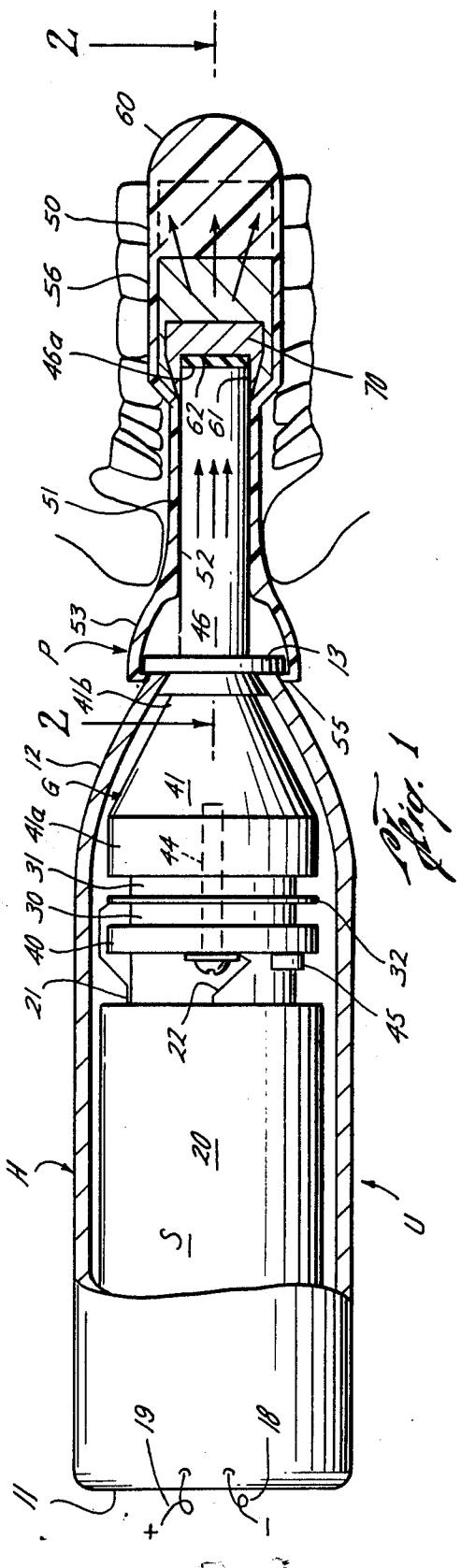
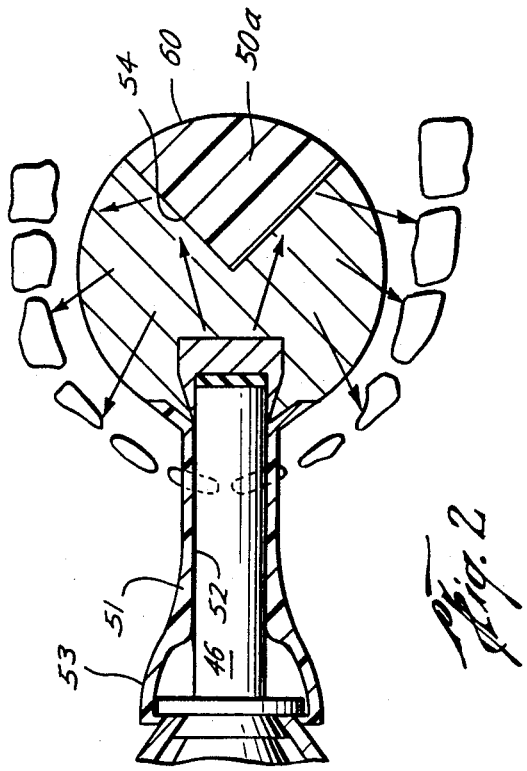
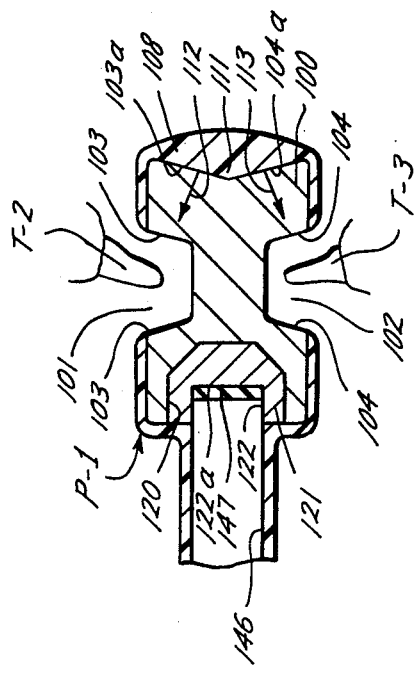

ULTRASONIC TOOTH CLEANER

BACKGROUND OF THE INVENTION

Heretofore various ultrasonic devices have been used for removing plaque and for cleaning teeth. However, such devices have typically used a pick which scratches or scrapes the surface of the teeth to remove plaque from the teeth. These ultrasonic devices move a scraper point at ultrasonic frequencies to scrape plaque from the teeth. Such device typically requires a skilled operator, such as a dentist or dental technician, and is not designed for self-use by untrained operators.

Examples of devices of this type are found in patents, such as U.S. Pat. No. 3,703,037 for "Ultrasonic Dental Hand-Piece With Detachable Treatment Tools" and U.S. Pat. No. 3,924,335 for "Ultrasonic Dental And Other Instrument Means And Methods".

Although ultrasonic cleaning devices have been available for cleaning jewelry and other metallic parts for many years, as far as is known to Applicants, no passive probe ultrasonic plaque remover has been available for removing plaque from teeth without a metal scaler, brush or other solid device for engaging the surface of the teeth.

SUMMARY OF THE INVENTION

The present invention provides a method and apparatus for cleaning teeth and removing plaque from teeth without requiring a specially trained operator. Such device includes an ultrasonic probe which is coupled with a liquid couple for transmitting ultrasonic energy to the surface of the teeth in a uniformly distributed pattern to break loose the bond between uniform plaque and the tooth surface. With this device, the ultrasonic energy is directed to specific areas with the maximum ultrasonic energy focused on the surfaces to be cleaned and with substantially less ultrasonic energy impinging on other surfaces of the oral cavity. Such device includes a passive probe adapted to be inserted into the mouth of the user and operated for a predetermined time interval to apply a desired level of ultrasonic energy to the teeth. The device includes both an ultrasonic generation device which is positioned outside of the mouth and an ultrasonic distribution device or passive probe which is inserted into the mouth. The ultrasonic distribution device is removably mounted on the ultrasonic generation device so that each person can have his personal in-mouth probe. Also, the ultrasonic probe includes an acoustical mirror which directs the sonic energy in the direction of the teeth to be cleaned and particularly the gap between adjacent teeth and away from other areas in the oral cavity. With a suitable liquid cleaner in the mouth, the probe is inserted into the mouth and actuated for a predetermined interval to provide a level of acoustic power at the surface of the teeth to remove plaque therefrom.

BRIEF DESCRIPTION OF THE DRAWINGS

FIG. 1 is an elevation view, partly in section, showing details of construction of the probe inserted in position in an oral cavity;

FIG. 2 is a plane view, partly in elevation and partly in section, taken on line 2—2 of FIG. 1 showing the probe inserted in an oral cavity; and FIG. 3 is an elevation of an alternate probe apparatus shown positioned between upper and lower teeth in an oral cavity.

DETAILED DESCRIPTION OF THE PREFERRED EMBODIMENT

The ultrasonic tooth cleaning apparatus of the present invention is designated generally U in FIG. 1 of the drawings. As shown, it includes a hollow tubular handle H with an oral probe P projecting from one end thereof for insertion into the oral cavity to distribute ultrasonic energy throughout the mouth. As will be explained in detail, the probe P is removable to permit a plurality of probes to be used with a single handle H so each family member can have a personal probe. Further, the handle H contains a power supply S for driving the ultrasonic generator G which is also contained in the handle. The probe may be inserted into a person's mouth which contains a mouthfull of liquid for coupling the probe with the teeth without touching or direct contacting the teeth and ultrasonic energy is transmitted throughout the mouth for a predetermined period of time to clean the teeth and to remove plaque therefrom.

Considering now the apparatus of the present invention in more detail, the handle H is a longitudinally extending hollow tubular body formed of plastic or other suitable electrical insulating material which is relatively lightweight and easily held in the hand. The outer end 11 is closed with some suitable closure means and the forward end has a tapered portion 12 which surrounds the horn and conforms generally to its shape. The tubular body terminates with an annular shoulder 13 which is provided for securing the removable probe P to the handle H.

In the preferred embodiment, the power supply S comprises a power oscillator 20 which is connected to a source of AC power by leads 18 and 19 and which is connected to the ultrasonic energy generator G by means of leads 21 and 22.

The ultrasonic energy generator G, which is mounted in the handle H, comprises a resonant ultrasonic transducer which is a single stack formed of a pair of piezoelectric driver discs 30 and 31 and a metal shim conductor 32 positioned therebetween. The piezoelectric disc stack is positioned between a biased load clamping plate 40 and a solid resonant ultrasonic horn 41. The discs 30 and 31 are secured between clamping plate 40 and the horn 41 by means of a bolt 44 which extends through suitable openings in each of the piezoelectric driver discs 30 and 31 as well as the metal shim conductor 32. The metal shim conductor is connected by lead 21 to the positive output of the power supply and the clamping plate 40 is connected to the negative lead from the power supply 24. A crystal sensor feedback pick-up 45 provides a signal feedback which is transmitted to the power oscillator to adjust or control its output frequency. In a preferred embodiment of this invention, the pair of discs are formed of lead zirconate-titanate material. These are mechanically clamped together with the common electrode 32 and are mass loaded with a biased pressure across the discs to provide maximum efficiency and eliminate the need for adhesives which may deteriorate or age.

The ultrasonic horn 41 has a cylindrical base portion 41a which engages the front of the resonant transducer and has a slightly larger diameter than disc 31. The horn also has a tapered conical portion 41b which reduces the area of the base to that of the ultrasonic coupling rod or shaft 46 which projects outwardly from the tapered horn portion and extends beyond the end of the handle H. The rod 46 is inserted into the passage or opening in the probe when it is attached to the handle as will be described in detail. The length of the sonic rod portion 46 is sized so as to provide a node (minimum amplitude) at the tapered horn at the location through which attachment is made between the ultrasonic device and the hand held case to eliminate unwanted vibration from the case. Further, the ultrasonic coupling rod 46 which projects from the tapered horn portion is terminated at the opposite end by the circular radiating surface 46a of the diameter of the rod. This radiating surface emits acoustical energy along the axis of the rod. Such sonic energy is thereafter redirected by the head of the probe as will be described.

The removable probe comprises a substantially flat disc-shaped head portion 50 which is supported on the end of a longitudinally extending hollow tubular neck or body 51 and which is adapted to be inserted into a person's mouth and to lie flat on or slightly above the tongue. The tubular body 51 has a cylindrical passage 52 into which the cylindrical sonic rod 46 is inserted when the probe is on the handle. A tapered or flared skirt 53 is provided at the opposite end of the body 51 from the head 50. The annular skirt 53 is provided with a lip 55 which extends radially inwardly of the skirt 53 for engaging the collar 13 for releasably securing the probe P on the handle H. The body and head of the probe P are preferably formed of a suitable plastic material, such as Plexiglas or an ABS high density plastic, having substantially the same acoustical impedance as water so that ultrasonic sound transmitted through the head from the radiating surface of the ultrasonic rod travels in plane waves and there is no significant reflection at the outer surface of the head 50. This provides the desirable acoustic characteristics of the head 50 and also enables the annular skirt 53 to flex sufficiently to allow the lip 55 to be snapped over the shoulder 13 for connecting and disconnecting the probe P from the handle H.

As shown, the head 50 is provided with an acoustical reflector or mirror which consists of a wedge-shaped plastic/air interface formed by a recess 50a in the plastic head 50 which recess is filled with foam insulation material 60. The wedge-shaped recess forms "V"-shaped plastic/air interface 54 which redirects the sonic energy outwardly toward the inner surface of the teeth T. This reflector 60 redirects the energy from the ultrasonic generator to the teeth and prevents such ultrasonic energy from passing further along the axis of the rod 46 which, when the probe is in use, would be directed toward the back of the user's throat.

As an alternative to the acoustical mirror shown in FIG. 2, a plurality of air pockets or voids can be distributed or arranged in the probe head 50 to deflect the sonic energy away from the longitudinal axis of the probe and away from the user's throat and toward the teeth T. An acoustical diffraction grating can also be used in the probe head to deflect the same energy and divert it away from the user's throat.

Further, the upper and lower surfaces 56 of the head 50 are preferably covered with foam insulation to prevent the sonic energy from being deflected or reflected upwardly towards the roof of the person's mouth or downwardly towards the person's tongue and throat. Thus, with this construction it will be appreciated that the ultrasonic energy is directed primarily at the teeth and at the gaps between the teeth to facilitate plaque removal.

A metallic insert 70 is provided in the head 50 to transmit sonic energy throughout the head. Such insert is provided with a cylindrical opening or passage 61 for receiving the tip of the sonic rod 46. Further, a disc 62, formed of rubber or other suitable elastomeric material, is positioned so as to fill the end opening 61 in the insert to provide a compressible connector for connecting the end of the rod 46 to the insert 70. Such disc 62 may be formed of some compressible material, such as rubber, and may be coated with a greaselike material, such as a silicone grease or petroleum jelly, to eliminate any air pockets and to facilitate the transmission of sonic energy to the head 50. It is important to exclude air from the area adjacent the tip of the rod to provide efficient transmittance of ultrasonic energy from the end of the shaft 46 to the head 50.

A liquid couplant solution is used with the sonic generator for transmitting sonic energy in the person's mouth from the probe to the teeth without any mechanical contact between the probe and the teeth; the sonic couplant solution being the energy carrier to the teeth. The liquid couplant solution is a solution which is suitable for use in the mouth and may be flavored, if desired.

With the apparatus of the present invention as shown in FIG. 1, the user may substantially fill his mouth with a suitable liquid couple and insert the head 50 between the lips into a position in the oral cavity behind the front teeth and with the lips closed about the neck of the probe P. The ultrasonic generator G is actuated to clean the teeth. It will be appreciated that a suitable timer (not shown) may be used to time the cleaning action to a predetermined amount to provide a safe and efficient cleaning pulse for cleaning teeth.

The ultrasonic generator of the present invention is designed to provide ultrasonic energy for freeing plaque from the surface of the teeth. Further, it will be appreciated that the plastic head 50 is designed to bring the sonic source close to the teeth for transmission through the surrounding liquid couple.

Considering the alternate embodiment of the head of the cleaning probe P-1 as shown in FIG. 3 of the drawings, the head includes a central body 100 having upper and lower transverse grooves 101 and 102, respectively, for receiving the upper teeth T-2 and the lower teeth T-3 when the head is inserted partially into the oral cavity. The upper and lower grooves 101 and 102, respectively, are provided with a pair of tapered walls 103 and 104, respectively, for directing the sonic energy toward the teeth when positioned in the grooves 101 and 102 as shown. The body 100 is formed of ABS plastic or other suitable rigid material which has approximately the same acoustical impedence as water. As shown, the body 100 is provided with a pair of inclined surfaces 103a which is substantially parallel to the surface 103 and another surface 104a which is inclined so as to be substantially parallel to the surface 104. The inner end of the probe P-1 is covered with a layer of foam material 108 which fills the recess 111 formed by the inclined surfaces 103a and 104a, to provide an air/plastic interface reflector for directing sonic energy in the directions indicated by the arrows 112 and 113.

The body 100 is also provided with a suitable recess 120 for receiving a metallic plug or insert 121 which is provided with a cylindrical opening 122 for receiving the tip end of the sonic generating rod 146. As shown, a rubber or elastomer pad 147 is positioned in the cylindrical opening 122 adjacent to the end 122a to provide a couple for coupling the end of the sonic rod 146 with the surrounding metal insert 121 to facilitate the transmission of sonic energy to the body 100 and to minimize wear at the end of the rod 146. It will be appreciated that the rubber or elastomer pad 147 may be coated with a greaselike material, such as silicone grease or petroleum jelly to eliminate any air pockets which would reduce the efficiency of the operation of the sonic rod 146.

It will be appreciated that in use the alternate embodiment shown in FIG. 3 of the drawings will be scanned or swept from side to side of the mouth for cleaning both the inner and outer surfaces of the teeth T without removing the probe P-1 from the mouth. Further, it will be appreciated that the cleaning is affected by directing sonic energy into the grooves 101 and 102 for cleaning the teeth T-2 and T-3 when positioned therein. Further, the handle H and the sonic generator G, as shown in FIG. 1 of the drawings, may also be used with the FIG. 3 embodiment and that the probe P-1 is provided with a connecting skirt (not shown), such as that illustrated at 53 in FIG. 1 of the drawings for connecting the probe P-1 to the handle H.

In another alternate embodiment of the present invention, a rechargeable battery power source may be used in lieu of the AC power supply in which case the rechargeable battery may be mounted in the handle H and then the cleaner will be self-contained.

The foregoing disclosure and description of the invention are illustrative and explanatory thereof, and various changes in the size, shape, and materials as well as in the details of the illustrated construction may be made without departing from the spirit and scope of the invention.

What is claimed is:

1. An ultrasonic tooth cleaning device comprising:
   (a) a hand held housing mounting an ultrasonic energy generator adapted to be positioned outside the mouth;
   (b) a power supply connected to said ultrasonic energy generator; and
   (c) ultrasonic distributor means driven by said ultrasonic energy generator connected to said housing and terminating in a continuous, unbroken, hard, radiating surface adapted to be inserted through a lip seal into a person's mouth containing a liquid couplant for ultrasonically cleaning the person's teeth when said radiating surface is positioned in close proximity to said teeth, said ultrasonic distributor means including a longitudinally extending hollow tubular body having a head at one end and having pper and lower transversely extending grooves for receiving upper and lower teeth when said head is inserted into the oral cavity and having acoustical mirror means-at one end thereof for impeding the flow of sonic energy axially of said longitudinally extending body and for redirecting such ultrasonic energy toward said transversely extending grooves.

2. An ultrasonic tooth cleaning device comprising:
   (a) a hand held housing mounting an ultrasonic energy generator adapted to be positioned outside the mouth;
   (b) a power supply connected to said ultrasonic energy generator;
   (c) ultrasonic distributor means driven by said ultrasonic energy generator connected to said housing and terminating in an oral probe having a continuous, unbroken, hard, radiating surface adapted to be inserted through a ip seal into a person's mouth containing a liquid couplant for ultrasonically cleaning the person's teeth when said radiating surface is positioned in close proximity to said teeth, said ultrasonic distributor including a resonant ultrasonic horn having a longitudinally extending rod which projects into said oral probe; and
   a metallic insert for transmitting sonic energy from the end of said longitudinally extending rod.

3. An ultrasonic tooth cleaning device comprising:
   (a) a hand held housing mounting an ultrasonic energy generator adapted to be positioned outside the mouth;
   (b) a power supply connected to said ultrasonic energy generator;
   (c) ultrasonic distributor means driven by said ultrasonic energy generator connected to said housing and terminating in an oral a probe having a continuous, unbroken, hard, radiating surface adapted to be inserted through a lip seal into a person's mouth containing a liquid couplant for ultrasonically cleaning the person's teeth when said radiating surface is positioned in close proximity to said teeth, said ultrasonic distributor means including a resonant ultrasonic horn having a longitudinally extending rod which projects into said oral probe; and
   an elastomeric insert positioned between the end of said rod and said oral probe.

* * * * *